(12) United States Patent
Rick et al.

(10) Patent No.: US 8,377,057 B2
(45) Date of Patent: *Feb. 19, 2013

(54) COOL-TIP COMBINED ELECTRODE INTRODUCER

(75) Inventors: Kyle R. Rick, Boulder, CO (US); David N. Heard, Boulder, CO (US); Steven P. Buysse, Longmont, CO (US)

(73) Assignee: Covidien AG (CH)

( * ) Notice: Subject to any disclaimer, the term of this patent is extended or adjusted under 35 U.S.C. 154(b) by 168 days.

This patent is subject to a terminal disclaimer.

(21) Appl. No.: 12/839,849

(22) Filed: Jul. 20, 2010

(65) Prior Publication Data

US 2010/0292686 A1 Nov. 18, 2010

Related U.S. Application Data

(63) Continuation of application No. 11/238,204, filed on Sep. 29, 2005, now Pat. No. 7,776,035.

(60) Provisional application No. 60/617,337, filed on Oct. 8, 2004.

(51) Int. Cl.
*A61B 18/14* (2006.01)
(52) U.S. Cl. ........................................ 606/41
(58) Field of Classification Search ...................... 606/41
See application file for complete search history.

(56) References Cited

U.S. PATENT DOCUMENTS

| | | |
|---|---|---|
| 2,031,682 A | 2/1936 | Frederick et al. |
| 4,074,718 A | 2/1978 | Morrison, Jr. |
| D263,020 S | 2/1982 | Rau, III |
| 4,375,220 A | 3/1983 | Matvias |
| 4,411,266 A | 10/1983 | Cosman |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| D295,893 S | 5/1988 | Sharkany et al. |
| D295,894 S | 5/1988 | Sharkany et al. |
| 4,826,487 A | 5/1989 | Winter |
| 4,832,024 A | 5/1989 | Boussignac et al. |
| 4,880,719 A | 11/1989 | Murofushi et al. |
| 4,961,435 A | 10/1990 | Kitagawa et al. |
| 4,966,597 A | 10/1990 | Cosman |
| 4,993,430 A | 2/1991 | Shimoyama et al. |
| 5,029,588 A | 7/1991 | Yock et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Lee S Cohen

(57) ABSTRACT

The present disclosure relates to systems, devices and methods for positioning and placing multiple electrodes in a target surgical site. An introducer is provided for facilitating the insertion of a cluster of electrodes into the body of a patient for performing tissue ablation. The introducer includes a body portion including a plurality of holes formed therein for selectively receiving a respective elongated shaft of the electrodes therethrough, wherein the holes of the introducer orient and space each electrode relative to one another, wherein the introducer includes a centrally disposed hole formed therein for receiving a guide needle therethrough.

16 Claims, 6 Drawing Sheets

U.S. PATENT DOCUMENTS

| | | | |
|---|---|---|---|
| 5,103,804 A | 4/1992 | Abele et al. |
| 5,230,623 A | 7/1993 | Guthrie et al. |
| 5,233,515 A | 8/1993 | Cosman |
| 5,246,438 A | 9/1993 | Langberg |
| 5,267,994 A | 12/1993 | Gentelia et al. |
| 5,281,213 A | 1/1994 | Milder et al. |
| 5,323,778 A | 6/1994 | Kandarpa et al. |
| 5,330,470 A | 7/1994 | Hagen |
| 5,330,518 A | 7/1994 | Neilson et al. |
| 5,334,193 A | 8/1994 | Nardella |
| 5,342,357 A | 8/1994 | Nardella |
| 5,348,554 A | 9/1994 | Imran et al. |
| 5,370,675 A | 12/1994 | Edwards et al. |
| 5,383,876 A | 1/1995 | Nardella |
| 5,383,917 A | 1/1995 | Desai et al. |
| 5,385,148 A | 1/1995 | Lesh et al. |
| 5,403,311 A | 4/1995 | Abele et al. |
| 5,409,000 A | 4/1995 | Imran |
| 5,409,006 A | 4/1995 | Buchholtz et al. |
| 5,417,686 A | 5/1995 | Peterson et al. |
| 5,433,739 A | 7/1995 | Sluijter et al. |
| 5,437,662 A | 8/1995 | Nardella |
| 5,458,597 A | 10/1995 | Edwards et al. |
| 5,462,521 A | 10/1995 | Brucker et al. |
| 5,472,441 A | 12/1995 | Edwards et al. |
| 5,490,850 A | 2/1996 | Ellman et al. |
| 5,500,012 A | 3/1996 | Brucker et al. |
| 5,520,684 A | 5/1996 | Imran |
| 5,536,267 A | 7/1996 | Edwards et al. |
| 5,571,147 A | 11/1996 | Sluijter et al. |
| 5,575,798 A | 11/1996 | Koutrouvelis |
| 5,588,432 A | 12/1996 | Crowley |
| 5,599,345 A | 2/1997 | Edwards et al. |
| 5,643,197 A | 7/1997 | Brucker et al. |
| 5,647,871 A | 7/1997 | Levine et al. |
| 5,662,111 A | 9/1997 | Cosman |
| 5,688,267 A | 11/1997 | Panescu et al. |
| 5,735,847 A | 4/1998 | Gough et al. |
| 5,775,338 A | 7/1998 | Hastings |
| 5,792,146 A | 8/1998 | Cosman |
| 5,848,967 A | 12/1998 | Cosman |
| 5,849,011 A | 12/1998 | Jones et al. |
| 5,868,740 A | 2/1999 | LeVeen et al. |
| 5,921,982 A | 7/1999 | Lesh et al. |
| 5,943,719 A | 8/1999 | Feldman et al. |
| 5,951,546 A | 9/1999 | Lorentzen |
| 6,001,093 A | 12/1999 | Swanson et al. |
| 6,006,126 A | 12/1999 | Cosman |
| 6,053,912 A | 4/2000 | Panescu et al. |
| D424,694 S | 5/2000 | Tetzlaff et al. |
| D425,201 S | 5/2000 | Tetzlaff et al. |
| 6,059,780 A | 5/2000 | Gough et al. |
| 6,061,551 A | 5/2000 | Sorrells et al. |
| 6,074,389 A | 6/2000 | Levine et al. |
| 6,080,149 A | 6/2000 | Huang et al. |
| 6,106,524 A | 8/2000 | Eggers et al. |
| 6,132,426 A | 10/2000 | Kroll |
| 6,146,380 A | 11/2000 | Racz et al. |
| 6,162,216 A | 12/2000 | Guziak et al. |
| 6,241,725 B1 | 6/2001 | Cosman |
| 6,246,912 B1 | 6/2001 | Sluijter et al. |
| 6,287,305 B1 | 9/2001 | Heim et al. |
| D449,886 S | 10/2001 | Tetzlaff et al. |
| 6,306,132 B1 | 10/2001 | Moorman et al. |
| 6,337,998 B1 | 1/2002 | Behl et al. |
| D457,958 S | 5/2002 | Dycus et al. |
| D457,959 S | 5/2002 | Tetzlaff et al. |
| 6,432,070 B1 | 8/2002 | Talish et al. |
| 6,478,793 B1 | 11/2002 | Cosman et al. |
| 6,506,189 B1 | 1/2003 | Rittman, III et al. |
| 6,530,922 B2 | 3/2003 | Cosman et al. |
| 6,537,272 B2 | 3/2003 | Christopherson et al. |
| 6,575,969 B1 | 6/2003 | Rittman, III et al. |
| 6,605,085 B1 | 8/2003 | Edwards |
| 6,613,047 B2 | 9/2003 | Edwards |
| 6,673,070 B2 | 1/2004 | Edwards et al. |
| 6,685,729 B2 | 2/2004 | Gonzalez |
| 6,706,050 B1 | 3/2004 | Giannadakis |
| D496,997 S | 10/2004 | Dycus et al. |
| D499,181 S | 11/2004 | Dycus et al. |
| 6,918,907 B2 | 7/2005 | Kelly et al. |
| 7,008,421 B2 | 3/2006 | Daniel et al. |
| D525,361 S | 7/2006 | Hushka |
| D531,311 S | 10/2006 | Guerra et al. |
| 7,137,980 B2 | 11/2006 | Buysse et al. |
| D533,942 S | 12/2006 | Kerr et al. |
| D535,027 S | 1/2007 | James et al. |
| 7,156,842 B2 | 1/2007 | Sartor et al. |
| 7,169,146 B2 | 1/2007 | Truckai et al. |
| 7,179,255 B2 | 2/2007 | Lettice et al. |
| 7,186,222 B1 | 3/2007 | Callister et al. |
| D541,418 S | 4/2007 | Schechter et al. |
| 7,207,989 B2 | 4/2007 | Pike, Jr. et al. |
| D541,938 S | 5/2007 | Kerr et al |
| 7,218,958 B2 | 5/2007 | Rashidi |
| 7,235,070 B2 | 6/2007 | Vanney |
| 7,235,073 B2 | 6/2007 | Levine et al. |
| 7,238,184 B2 | 7/2007 | Megerman et al. |
| 7,264,619 B2 | 9/2007 | Venturelli |
| 7,278,991 B2 | 10/2007 | Morris et al. |
| 7,282,049 B2 | 10/2007 | Orszulak |
| 7,294,127 B2 | 11/2007 | Leung et al. |
| 7,294,143 B2 | 11/2007 | Francischelli |
| 7,302,285 B2 | 11/2007 | Fuimaono et al. |
| 7,303,558 B2 | 12/2007 | Swanson |
| 7,331,947 B2 | 2/2008 | McGuckin, Jr. et al. |
| RE40,156 E | 3/2008 | Sharps et al. |
| D564,662 S | 3/2008 | Moses et al. |
| 7,341,586 B2 | 3/2008 | Daniel et al. |
| 7,344,533 B2 | 3/2008 | Pearson et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,387,625 B2 | 6/2008 | Hovda et al. |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,587 B2 | 9/2008 | Bek et al. |
| 7,480,533 B2 | 1/2009 | Cosman et al. |
| 7,553,309 B2 | 6/2009 | Buysse |
| D613,412 S | 4/2010 | DeCarlo |
| 7,744,606 B2 | 6/2010 | Miller et al. |
| 7,763,018 B2 | 7/2010 | DeCarlo et al. |
| 7,776,035 B2 | 8/2010 | Rick et al. |
| 2002/0156472 A1 | 10/2002 | Lee et al. |
| 2004/0267256 A1* | 12/2004 | Garabedian et al. ............ 606/41 |
| 2005/0096681 A1 | 5/2005 | Desinger et al. |
| 2005/0155743 A1 | 7/2005 | Getz, Jr. et al. |
| 2006/0122627 A1* | 6/2006 | Miller et al. .................. 606/129 |
| 2007/0260240 A1 | 11/2007 | Rusin |
| 2008/0021448 A1 | 1/2008 | Orszulak |
| 2008/0183165 A1 | 7/2008 | Buysse et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |

| | | |
|---|---|---|
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 171 967 | 2/1986 |
| EP | 0 246 350 | 11/1987 |
| EP | 0 310 431 | 4/1989 |
| EP | 0 521 264 | 1/1993 |
| EP | 0 556 705 | 8/1993 |
| EP | 0 558 429 | 9/1993 |
| EP | 0 608 609 | 8/1994 |
| EP | 0 836 868 | 4/1998 |
| EP | 0 882 955 | 12/1998 |
| EP | 1 070 518 | 1/2001 |
| EP | 1 159 926 | 5/2001 |
| EP | 1 465 037 | 10/2004 |
| EP | 1645234 | 4/2006 |
| EP | 1656900 | 5/2006 |
| FR | 179 607 | 11/1906 |
| FR | 1 275 415 | 10/1961 |
| FR | 1 347 865 | 11/1963 |
| FR | 2 235 669 | 1/1975 |
| FR | 2 278 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 99/01074 | 1/1999 |
| WO | WO 99/04710 | 2/1999 |
| WO | WO 99/22657 | 5/1999 |
| WO | WO 00/67846 | 11/2000 |
| WO | WO 01/00114 | 1/2001 |
| WO | WO 2004/045436 | 6/2004 |
| WO | WO 2005/009528 | 2/2005 |
| WO | WO2010/035831 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. lnterv. Radio!, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite•Element Codes to Model Electrical Heating and Non•Linear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, " LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.

European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

COOL-TIP COMBINED ELECTRODE INTRODUCER

CROSS-REFERENCE TO RELATED APPLICATIONS

This application is a continuation of U.S. patent application Ser. No. 11/238,204, filed on Sep. 29, 2005 and issued on Aug. 17, 2010 as U.S. Pat. No. 7,776,035, which claims the benefit of and priority to U.S. Provisional Application No. 60/617,337, filed on Oct. 8, 2004, the entire contents of each of which are incorporated herein by reference.

BACKGROUND

1. Technical Field

The present disclosure relates generally to cluster ablation electrode systems and, more particularly, to systems, devices and methods for positioning and placing multiple electrodes in a target surgical site.

2. Background of Related Art

The use of radiofrequency electrodes for ablation of tissue in a patient's body is known. In a typical situation, a radiofrequency electrode comprising an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source, which provides radiofrequency voltage to the electrode, which transmits the radiofrequency current into the tissue near its exposed conductive tip. This current usually returns to the power source through a reference electrode, which may comprise a large area conductive contact connected to an external portion of the patient's body.

In some applications, for example, tumor ablation procedures, multiple electrodes are inserted into the body in an array to enlarge ablation volumes.

In a particular application, arrays of high frequency electrodes are inserted into tumors. The electrodes are typically placed in a dispersed fashion throughout the tumor volume to cover the tumor volume with uniform heat, typically below about 45° C. The electrodes may be sequentially applied with high frequency voltage so that each electrode heats in sequence its neighboring tissue and then shuts off. Then, the next electrode does the same in a time series. This sequence of cycling the voltage through the electrodes continues at a prescribed frequency and for a period of time.

The electrode systems discussed above are limited by the practical size of lesion volumes they produce. Accordingly, electrodes with cooled conductive tips have been proposed. With cooling, radiofrequency electrode tips generally produce larger lesion volumes compared with radiofrequency electrodes, which are not cooled. For example, standard single cylindrical electrodes, with cooled tips, as described above, may make lesion volumes up to 3 to 4 cm in diameter in living tissue (e.g., the liver) by using cannulae of 1 to 2 mm in diameter and having exposed tip lengths of several centimeters.

Desirably, a configuration of radiofrequency electrodes, which can accomplish ablation in the range of 4 to 6 cm diameter or greater for the purpose of adequately treating large cancerous tumors in the body are necessary to effectively destroy the tumor and combat cancerous cells from spreading. It is further necessary that such an electrode system involve a simple geometry, reduced numbers of tissue insertions, facilitate planning of needle placement, and facilitate planning of heat ablation geometry and distribution.

An electrode system, which can be easily inserted into an organ or through the skin with minimal risk of hemorrhage and discomfort to the patient, is desirable.

According to yet another aspect of the present disclosure, an introducer is provided for facilitating the insertion of a cluster of electrodes into the body of a patient for tissue for performing tissue ablation. The introducer includes a body portion including a plurality of holes formed therein for selectively receiving a respective elongated shaft of the electrodes therethrough, wherein the holes of the introducer orient and space each electrode relative to one another, wherein the introducer includes a centrally disposed hole formed therein for receiving a guide needle therethrough.

The introducer may further include a distal introducer including a plurality of arrays of hole clusters formed therein each arranged in a linear row, wherein the rows of hole clusters are equally spaced from one another; and a proximal introducer including a plurality of arrays of holes formed therein each arranged in a linear row, wherein the rows of holes are equally spaced from one another.

The holes of each radial row of holes of the proximal introducer may be equally spaced from one another. In an embodiment, the proximal introducer includes six arrays of holes formed, wherein the rows of holes of the proximal introducer alternate between rows of six holes and rows of seven holes.

Each cluster of holes of the distal introducer may include a radially inner-most hole and a pair of radially outer-most holes. The radially outer-most holes may be offset an angle from an axis extending through the inner-most holes of each respective array of hole clusters. The inner-most holes of each radial row of clusters of the distal introducer may be equally spaced from one another.

The distal introducer may include six arrays of clusters formed therein arranged in a linear row. The rows of clusters of the distal introducer may alternate between rows of six clusters and rows of seven clusters.

Systems or devices which facilitate the positioning and placement of the radiofrequency electrodes relative to one another and relative to the target tissue volume are also desirable.

SUMMARY

The present disclosure relates to systems, devices and methods for positioning and placing multiple electrodes in a target surgical site.

According to an aspect of the present disclosure an electrode system is provided for use with a high frequency generator to induce coherent high frequency heat ablation volumes within targeted tissue of a patient. The electrode system includes a hub and at least three electrodes. Each electrode includes a substantially rigid elongated shaft extending from the hub and terminating in a sealed distal end section having an exposed conductive tip portion configured to be inserted into the targeted tissue and adapted at a proximal end section to be coupled to a high frequency generator to simultaneously apply an equal output voltage to each of the exposed conductive tip portions. Each electrode further includes a closed-loop fluid communication channel pathway which includes an inflow opening adapted for connection to a coolant fluid supply, and a channel portion in fluid communication with the inflow opening. The channel portion extends distally inside the conductive tip portion to carry coolant to the inside of the conductive tip portion and further extends proximally back to an outlet opening adapted to carry coolant away from the conductive tip portion.

The electrode system further includes an introducer including a plurality of holes formed therein for selectively receiving a respective elongate shaft of the electrodes therethrough. The holes of the introducer orient and space each electrode relative to one another. The introducer includes a centrally disposed hole formed therein for receiving a guide needle therethrough.

The conductive tip portions of the at least three electrodes may be arrayed relative to each other in a predetermined non-linear geometric spatial relationship relative to a longitudinal axis of the instrument such that upon application of an output voltage to the conductive tip portions, a coherent ablation isotherm is generated which encloses a desired target volume of the tissue to induce a large heat ablation volume.

In an embodiment, the electrode receiving holes of the introducer are each equally spaced from the central hole of the introducer. Each electrode receiving hole of the introducer includes a longitudinal axis which is parallel to one another.

In an embodiment, the electrode system includes a distal introducer and a proximal introducer. The distal introducer and the proximal introducer may each include a central hole formed therein for selectively receiving a guide needle therethrough, wherein the central holes function to align the distal and proximal introducers with one another.

The proximal introducer may include a plurality of arrays of holes formed therein each arranged in a linear row. The rows of holes are desirably equally spaced from one another.

It is envisioned that the holes of each radial row of holes of the proximal introducer are equally spaced from one another. The proximal introducer includes six arrays of holes formed therein arranged in a linear row. In an embodiment, the rows of holes of the proximal introducer alternate between rows of six holes and rows of seven holes.

It is contemplated that the distal introducer includes a plurality of arrays of hole clusters formed therein each arranged in a linear row. The rows of hole clusters are desirably equally spaced from one another. Each cluster of holes of the distal introducer may include a radially inner-most hole and a pair of radially outer-most holes. The radially outer-most holes may be offset an angle from an axis extending through the inner-most holes of each respective array of hole clusters.

In an embodiment, the inner-most holes of each radial row of clusters of the distal introducer are equally spaced from one another. The distal introducer includes six arrays of clusters formed therein arranged in a linear row. The rows of clusters of the distal introducer alternate between rows of six clusters and rows of seven clusters.

According to another aspect of the present disclosure, a system for inducing enlargement of heat ablation volumes within tissue of a patient's body is provided. The system includes a high frequency generator for supplying an output voltage; at least three substantially rigid, elongated electrodes adapted to be inserted into the tissue of a patient's body; and an introducer including a plurality of holes formed therein for selectively receiving a respective elongate shaft of the electrodes therethrough. Each of the at least three electrodes has exposed conductive tip portions arranged in a predetermined parallel relationship and a closed-loop fluid communication channel pathway. The channel pathway includes an inflow opening adapted for connection to a coolant fluid supply, and a channel portion in fluid communication with the inflow opening. The channel portion extends distally inside the conductive tip portion to carry coolant to the inside of the conductive tip portion and further extends proximally back to an outlet opening adapted to carry coolant away from the conductive tip portion.

The holes of the introducer orient and space each electrode relative to one another. The introducer includes a centrally disposed hole formed therein for receiving a guide needle therethrough.

The introducer includes a distal introducer including a plurality of arrays of hole clusters formed therein each arranged in a linear row, wherein the rows of hole clusters are equally spaced from one another; and a proximal introducer including a plurality of arrays of holes formed therein each arranged in a linear row, wherein the rows of holes are equally spaced from one another.

The holes of each radial row of holes of the proximal introducer may be equally spaced from one another. The proximal introducer may include six arrays of holes formed. The rows of holes of the proximal introducer alternate between rows of six holes and rows of seven holes. Each cluster of holes of the distal introducer may include a radially inner-most hole and a pair of radially outer-most holes, wherein the radially outer-most holes may be offset an angle from an axis extending through the inner-most holes of each respective array of hole clusters. The inner-most holes of each radial row of clusters of the distal introducer may be equally spaced from one another. The distal introducer may include six arrays of clusters formed therein arranged in a linear row. The rows of clusters of the distal introducer may alternate between rows of six clusters and rows of seven clusters.

According to yet another aspect of the present disclosure, a process for heat ablation of tissue in a patient is provided. The process includes the steps of providing an electrode system for inducing enlargement of heat ablation volumes within tissue of a patient's body. The electrode system includes a high frequency generator for supplying an output voltage; at least three substantially rigid, elongated electrodes adapted to be inserted into the tissue of a patient's body; and an introducer including a plurality of holes formed therein for selectively receiving a respective elongate shaft of the electrodes therethrough. Each of the at least three electrodes has an exposed conductive tip portion arranged in a predetermined parallel relationship and a closed-loop fluid communication channel pathway. The channel pathway includes an inflow opening adapted for connection to a coolant fluid supply, and a channel portion in fluid communication with the inflow opening. The channel portion extends distally inside the conductive tip portion to carry coolant to the inside of the conductive tip portion and further extends proximally back to an outlet opening adapted to carry coolant away from the conductive tip portion.

The holes of the introducer orient and space each electrode relative to one another. The introducer includes a centrally disposed hole formed therein for receiving a guide needle therethrough.

The method further includes inserting the electrodes into desired holes of the introducer in order to position each electrode relative to one another; inserting the electrodes into the tissue; applying substantially the same radiofrequency output through the electrodes to a targeted tissue volume to produce coherent heating of the targeted tissue volume; raising the radiofrequency output to a level that induces enlargement of the volume of heat ablation in the tissue near the electrodes; and cooling each electrode by circulating a cooling fluid through a closed-loop fluid communication channel pathway formed in each of the electrodes.

It is envisioned that the introducer includes a distal introducer including a plurality of arrays of hole clusters formed therein each arranged in a linear row, wherein the rows of hole clusters are equally spaced from one another; and a proximal introducer including a plurality of arrays of holes formed therein each arranged in a linear row, wherein the rows of holes are equally spaced from one another.

The method further includes the steps of placing the electrodes into desired holes of the proximal introducer; placing the distal introducer in a desired position on the skin surface of the patient; introducing the electrodes into the patient through the holes provided in the distal introducer; and advancing the electrodes through the distal introducer.

The method may further include the steps of placing a guide needle into a central hole formed in the distal introducer; inserting the guide needle into the body of the patient such that a tip of the guide needle is placed in close proximity to a target tissue; and placing the distal introducer against the skin of the patient.

The method may further include the steps of withdrawing the guide needle from the distal introducer; and inserting the electrodes into the body of the patient through the holes formed in the distal introducer.

The method may still further include the step of advancing the electrodes through the distal introducer until the tips thereof are in close proximity to the target tissue.

For a better understanding of the present disclosure and to show how it may be carried into effect, reference will now be made by way of example to the accompanying drawings.

BRIEF DESCRIPTION OF THE DRAWINGS

Various preferred embodiments of the presently disclosed systems, devices and methods are disclosed herein with reference to the drawings wherein.

DETAILED DESCRIPTION OF PREFERRED EMBODIMENTS

Figure 1:
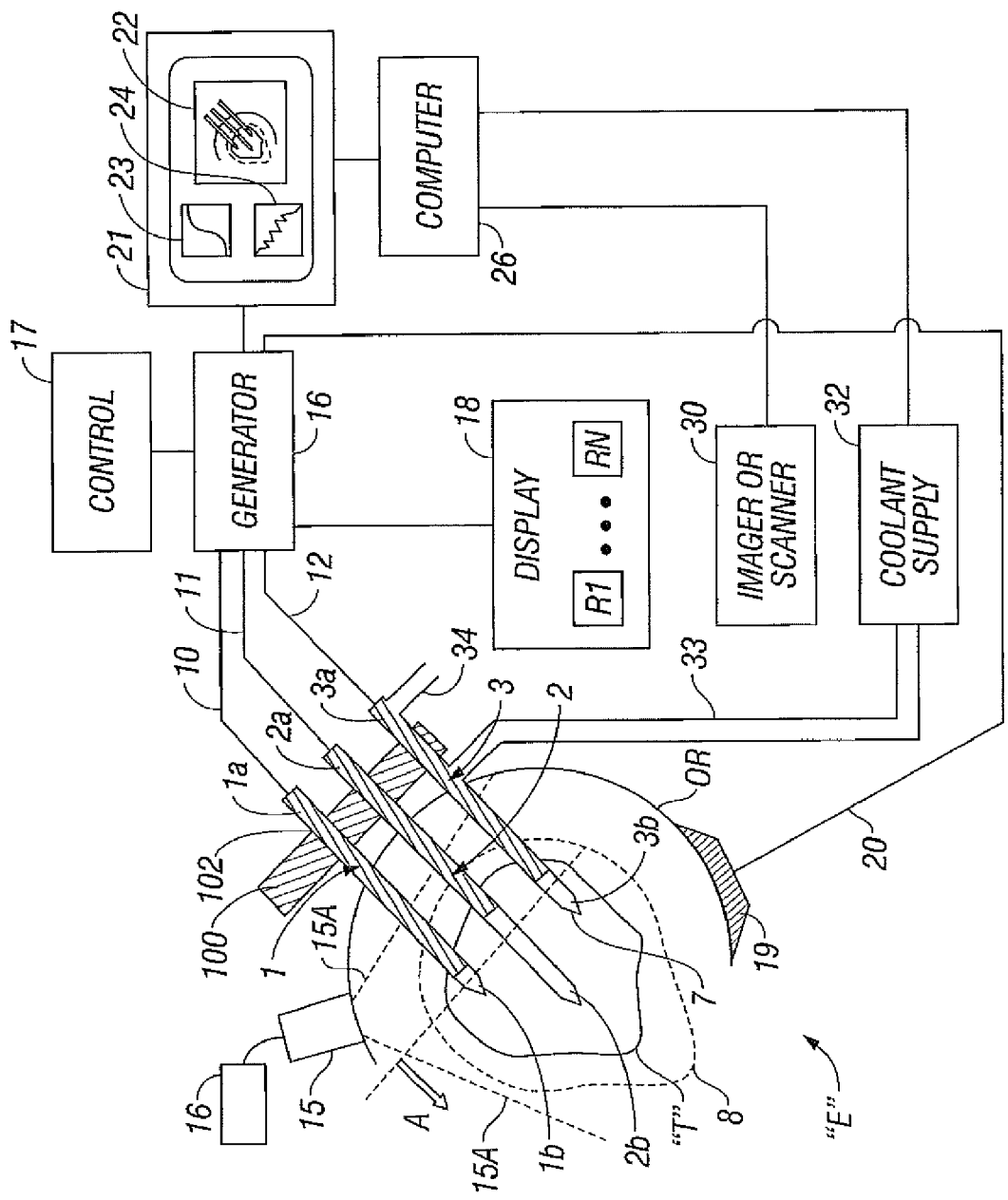
FIG. 1 is a schematic illustration of an ablation electrode array system according to the present disclosure showing multiple radiofrequency electrodes being positioned in a patient's organ for producing heat ablation of a targeted tissue area.

Referring initially to FIG. 1, an embodiment of a multiple electrode arrangement such as an ablation electrode array system, in accordance with the present disclosure, is generally designated "E". Electrode array system "E" includes a plurality of electrodes 1, 2 and 3, which are to be inserted into an organ "OR" of a human body or any other body tissue. Respective distal tips 1b, 2b and 3b of electrodes 1, 2 and 3 are un-insulated and conductively exposed so that electrical currents induce heating within the tissue or organ "OR". A targeted volume of tissue "T" is shown in sectional view and may represent, for example, a tumor or other abnormality in a human body.

Electrodes 1, 2 and 3 are connected by respective wires or cables 10, 11 and 12 to an electrosurgical generator 16. Electrosurgical generator 16 may be a radiofrequency or high frequency type generator. Electrosurgical generator 16 includes control elements, illustrated by block 17, which may, for example, increase the radiofrequency power output of electrodes 1, 2 and 3, control temperature when electrode array system "E" or satellite sensors (not shown) include temperature sensors, monitor or control impedance, power, current, voltage, or other output parameters. Electrosurgical generator 16 may include a display or screen, illustrated by block 18, within it or as a separate system, for providing a display of heating parameters such as temperature for one or more of electrodes 1, 2 and 3, impedance, power, current, or voltage of the radiofrequency output. Such individual display readings are illustrated by the reference letters R1 . . . RN.

Electrode system "E" further includes a reference electrode 19, which may be placed in contact with the skin of a patient or an external surface of organ "OR" with a connection 20 to electrosurgical generator 16. Reference electrode 19 and connection 20 serves as a path for return current from electrosurgical generator 16 through electrodes 1, 2 and 3.

Each electrode 1, 2 and 3 includes a rigid shaft 1a, 2a and 3a, respectively, which enables electrodes 1, 2 and 3 to be easily urged into the body tissue or organ "OR". Each electrode 1, 2 and 3 terminates pointed distal tips 1b, 2b and 3b, respectively. Desirably, a portion of the external surface of each electrode 1, 2 and 3 is covered with an insulating material, as indicated by hatched line areas in FIG. 1. Distal tips 1b, 2b and 3b are connected, through respective shafts 1a, 2a and 3a to cables 10, 11 and 12, respectively, and thereby to electrosurgical generator 16.

By way of example only and in no way to be considered as limiting, electrosurgical generator 16 may be a radiofrequency generator with frequency between about 100 kilohertz (kHz) to several hundred megahertz (MHz). Additionally, electrosurgical generator 16 may have power output ranging from several watts to several hundred watts, depending on the clinical application.

Desirably, electrodes 1, 2 and 3 may be raised to the same radiofrequency voltage potential from electrosurgical generator 16. The array of electrodes thus becomes, in effect, a larger, coherent electrode including the individual electrode tips 1b, 2b and 3b. Thus, the heating effect of the array of electrodes is substantially similar to that achieved by one large single electrode.

As seen in FIG. 1, by way of illustration only, a targeted region to be ablated is represented in sectional view by the line "T". It is desired to ablate the targeted region "T" by fully engulfing targeted region "T" in a volume of lethal heat elevation. The targeted region "T" may be, for example, a tumor which has been detected by an image scanner 30. For example, CT, MRI, or ultrasonic image scanners may be used, and the image data transferred to a computer 26. As an alternate example, an ultrasonic scanner head 15 may be disposed in contact with organ "OR" to provide an image illustrated by lines 15A. A data processor 16 may be connected to the display devices to visualize targeted region "T" and/or ablation zone "T1" in real time during the ablation procedure.

The image representation of the scan may be displayed on display unit 22 to represent the size and position of target region "T". Placement of electrodes 1, 2 and 3 may be predetermined based on such image data as interactively determined by real-time scanning of organ "OR". Electrodes 1, 2 and 3 are inserted into the tissue by freehand technique by a guide block or introducer 100 with multi-hole templates, or by stereotactic frame or frameless guidance, as known by those skilled in the art.

Desirably, an array of electrodes 1, 2 and 3 are connected to the same radiofrequency voltage from electrosurgical generator 16. Accordingly, the array of electrodes 1, 2 and 3 will act as a single effectively larger electrode. The relative position and orientation of electrodes 1, 2 and 3 enable the creation of different shapes and sizes of ablation volumes. For example, in FIG. 1, dashed line 8 represents the ablation isotherm in a sectional view through organ "OR". Such an ablation isotherm may be that of the surface achieving possible temperatures of approximately 50° C. or greater. At that temperature range, sustained for approximately 30 seconds to approximately several minutes, tissue cells will be ablated. The shape and size of the ablation volume, as illustrated by dashed line 8, may accordingly be controlled by the configuration of the electrode array, the geometry of the distal tips 1b, 2b and 3b of electrodes 1, 2 and 3, respectively, the amount of RF power applied, the time duration that the power is applied, cooling of the electrodes, etc.

Figure 2:
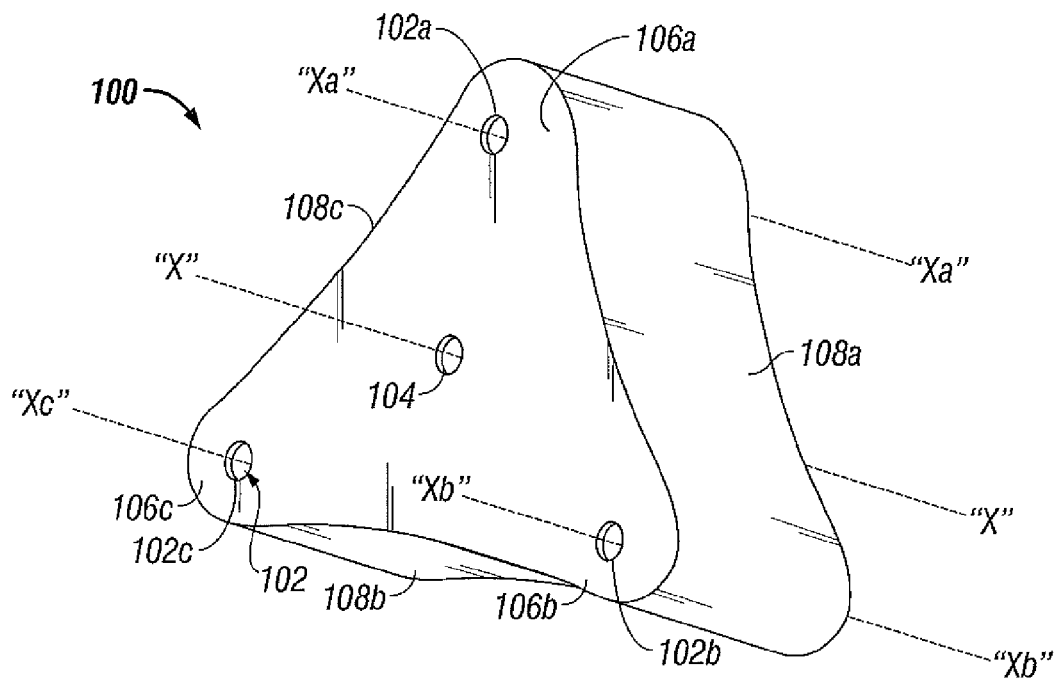
FIG. 2 is a perspective view of an electrode introducer according to an embodiment of the present disclosure.
Figure 3:
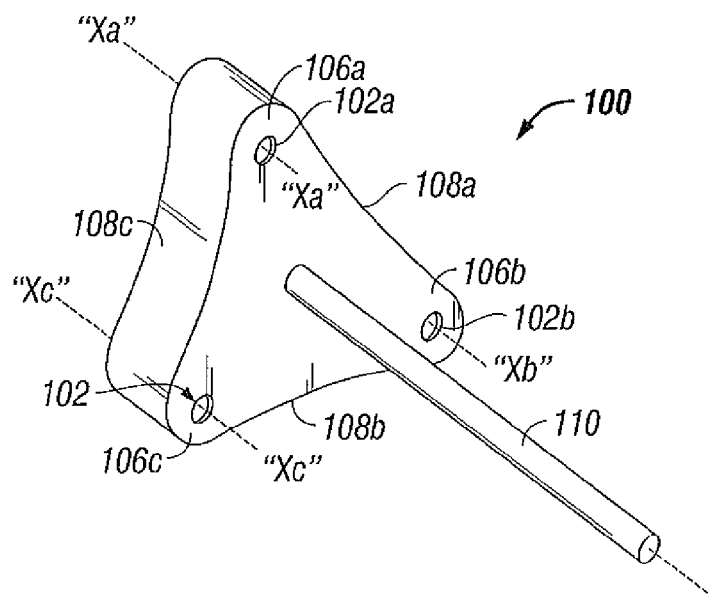
FIG. 3 is a perspective view of the electrode introducer of FIG. 2 including a needle extending therefrom.

Turning now to FIGS. 2 and 3, a guide block or introducer, in accordance with an embodiment of the present disclosure, is generally designated as 100. Introducer 100 includes a plurality of electrode through-holes 102 formed therein. Desirably, as seen in FIGS. 2 and 3, introducer 100 includes a first set of three holes 102a, 102b and 102c formed therein. Preferably, holes 102a, 102b and 102c are spaced an equal distance apart from one another. As such, holes 102a, 102b and 102c define an equilateral triangle. Each hole 102a, 102b and 102c defines a longitudinal axis "Xa, Xb and Xe". Preferably, longitudinal axes "Xa, Xb and Xc" are at least substantially parallel to one another. Desirably, holes 102a, 102b and 102c are sized and dimensioned to slidably receive a respective electrode 1, 2 and 3 therein.

With continued reference to FIGS. 2 and 3, introducer 100 further includes a central hole 104 formed therethrough. Central hole 104 defines a central longitudinal axis "X". Preferably, the central longitudinal "X" axis is at least substantially parallel to the longitudinal axes "Xa, Xb and Xc" of holes 102a, 102b and 102c. Desirably, central hole 104 is located at the intersection of axes or lines extending orthogonally through the longitudinal axes "Xa, Xb and Xe" of holes 102a, 102b and 102c.

As seen in FIGS. 2 and 3, introducer 100 may have a substantially triangular geometric configuration including corners 106a, 106b and 106c and side walls 108a, 108b and 108c. It is envisioned that a hole 102a, 102b and 102c is formed near a respective corner 106a, 106b and 106c of introducer 100. Desirably, each corner 106a, 106b and 106c of introducer 100 is rounded or radiused. Additionally, side walls 108a, 108b and 108c may be planar and, desirably, as seen in FIGS. 2 and 3, may be concave.

In accordance with the present disclosure, introducer 100 functions to hold or maintain electrodes 1, 2 and 3 of electrode system "E" substantially parallel to one another and at a defined distance from one another during the use thereof. It is envisioned that a guide needle 110 may be advanced through center hole 104 of introducer 100 and advanced to the desired target tissue using known medical imaging techniques (e.g., ultrasound, computer tomography, magnetic resonance imaging, X-ray, CT scan, etc.)

In one embodiment, as seen in FIG. 3, it is envisioned that center hole 104 may be eliminated and guide needle 110 may be operatively secured to the center of introducer 100 (i.e., at the central longitudinal "X" axis). In the present embodiment, introducer 100 may be introduced or advanced to the target tissue in a manner similar to that described above.

Figure 4:
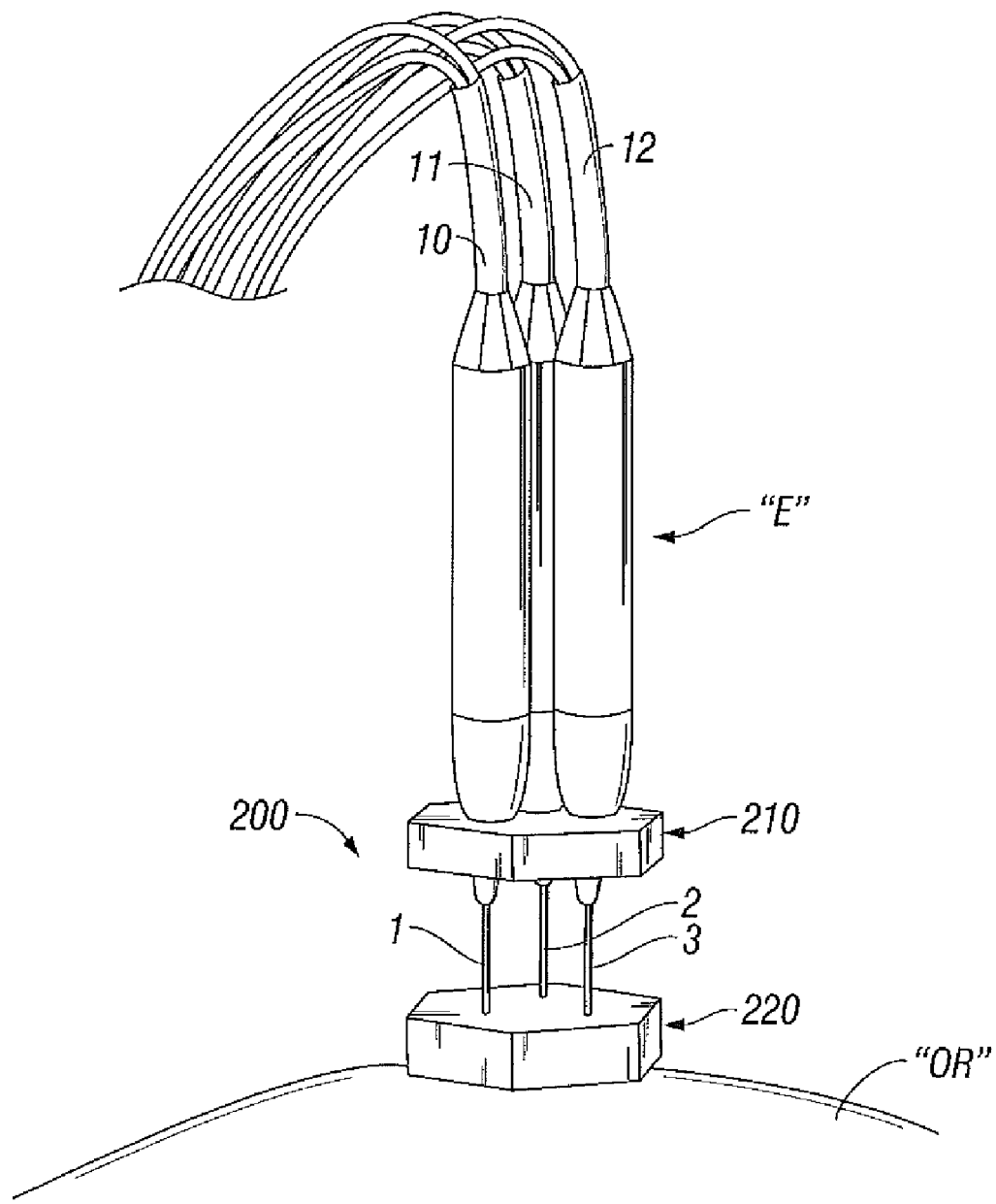
FIG. 4 is a perspective view of the electrode array system of FIG. 1 including a two piece combined electrode introducer according to another embodiment of the present disclosure.

Turning now to FIGS. 4-9, an introducer, in accordance with an alternative embodiment of the present disclosure, is generally designated as 200 and is shown in operative association with a cluster electrode system "E". Introducer 200 includes a first or proximal introducer 210 and a second or distal introducer 220. Desirably, as seen in FIG. 4, proximal introducer 210 and distal introducer 220 are used in cooperation with or in combination with one another to hold or maintain electrodes 1, 2 and 3 of electrode system "E" substantially parallel to one another, at a defined distance from one another and/or at a defines location relative to one another during the use thereof.

Figure 5:
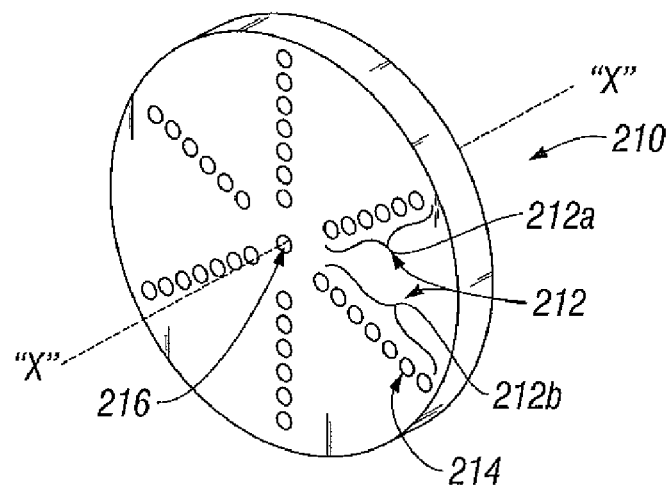
FIG. 5 is a perspective view of a first electrode introducer of the two piece combined electrode introducer shown in FIG. 4.
Figure 6:
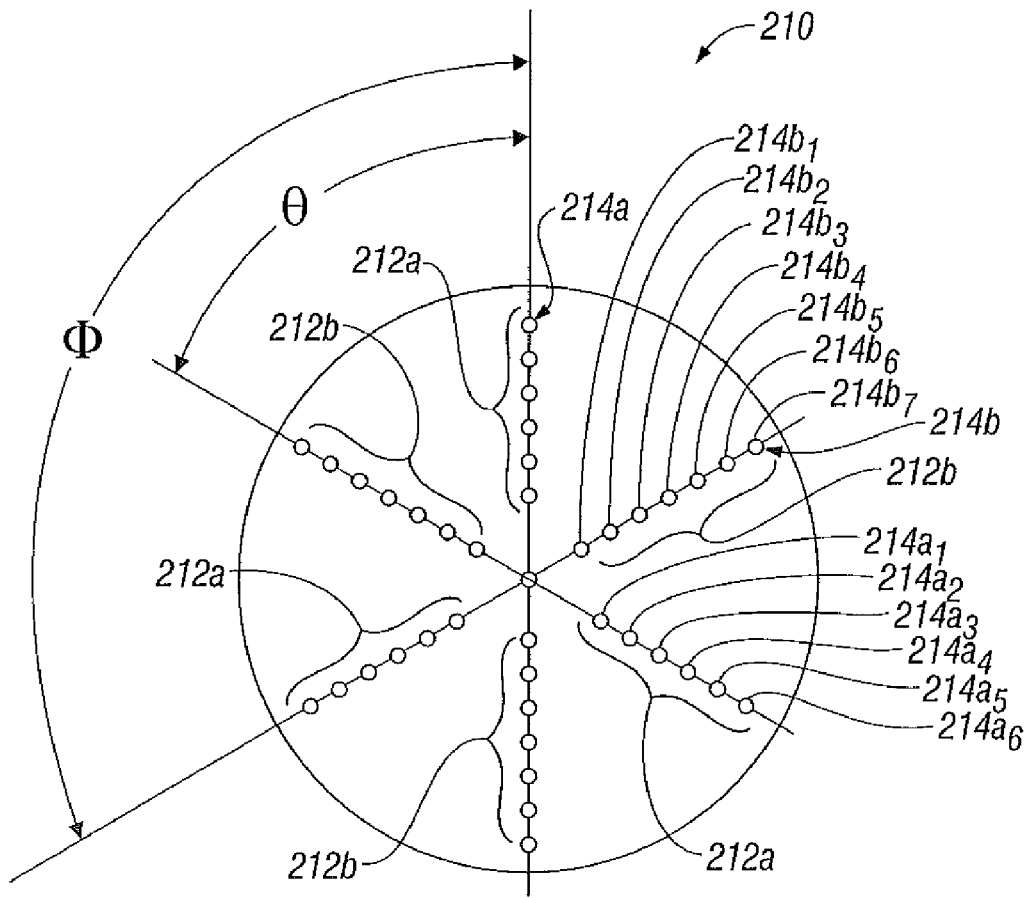
FIG. 6 is a top plan view of the first electrode introducer of FIG. 5.

Turning now to FIGS. 5 and 6, proximal introducer 210 includes a plurality of radially oriented rows 212 of holes 214 formed therein. Preferably, each row 212 is equally spaced from one another by an angle "Θ" relative to one another. As seen in FIGS. 5 and 6, proximal introducer 210 may include six (6) rows 212 of holes 214 which are spaced from one another by an angle "Θ" approximately equal to 60°. Desirably, each hole 214 includes a longitudinal axis which is at least substantially parallel to one another. In accordance with an embodiment of the present disclosure, each hole 214 may have a diameter of approximately 0.085 in. (2.16 mm)

Proximal introducer 210 further includes a central hole 216 formed therethrough. Central hole 216 defines a central longitudinal axis "X". Preferably, the central longitudinal "X" axis is at least substantially parallel to the longitudinal axes of holes 214. Desirably, central hole 216 is located at the intersection of rows 212.

As seen in FIGS. 5 and 6, a first set of rows 212a includes six (6) holes 214a formed therealong. Desirably, rows 212a of holes 214a are spaced from one another by an angle "Φ" approximately equal to 120°. A second set or rows 212b includes seven (7) holes 214b formed therealong. Desirably, rows 212b of holes 214b are spaced from one another by an angle "Φ" approximately equal to 120°.

Preferably, the respective holes 214a of the first set of rows 212a define an equilateral triangle therebetween. Accordingly, in one embodiment, the distance between respective inner-most holes $214a_1$ is approximately 0.984 in. (25.0 mm). The distance between respective second inner-most holes $214a_2$ is approximately 1.378 in. (35.0 mm). The distance between respective third inner-most holes $214a_3$ is approximately 1.772 in. (45.0 mm). The distance between respective fourth inner-most holes $214a_4$ is approximately 2.165 in. (55.0 mm). The distance between respective fifth inner-most holes $214a_5$ is approximately 2.559 in. (65.0 mm). The distance between respective sixth inner-most holes $214a_6$ is approximately 2.953 in. (75.0 mm).

Preferably, the respective holes 214b of the second set of rows 212b also define an equilateral triangle therebetween. Accordingly, in one embodiment, the distance between respective inner-most holes $214b_1$ is approximately 0.787 in. (20.0 mm). The distance between respective second inner-most holes $214b_2$ is approximately 1.181 in. (30.0 mm). The distance between respective third inner-most holes $214b_3$ is approximately 1.575 in. (40.0 mm). The distance between respective fourth inner-most holes $214b_4$ is approximately 1.969 in. (50.0 mm). The distance between respective fifth inner-most holes $214b_5$ is approximately 2.362 in. (60.0 mm). The distance between respective sixth inner-most holes $214b_6$ is approximately 2.756 in. (70.0 mm). The distance between respective seventh inner-most holes $214b_7$ is approximately 3.150 in, (80.0 mm).

Desirably, as seen in FIGS. 5 and 6, proximal introducer 210 may have a substantially circular geometric profile. In one embodiment, proximal introducer 210 may have a diameter approximately 4.0 in. (102.0 mm). It is further envisioned that proximal introducer 210 may have a thickness of approximately 0.38 in. (9.65 mm).

Figure 7:
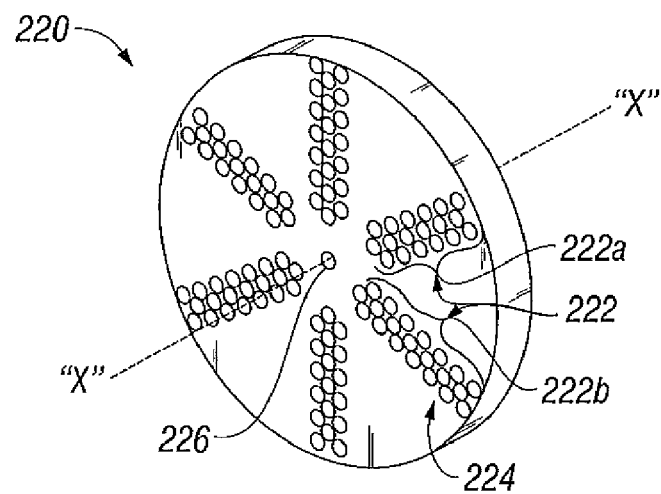
FIG. 7 is a perspective view of a second electrode introducer of the two piece combined electrode introducer shown in FIG. 4.
Figure 8:
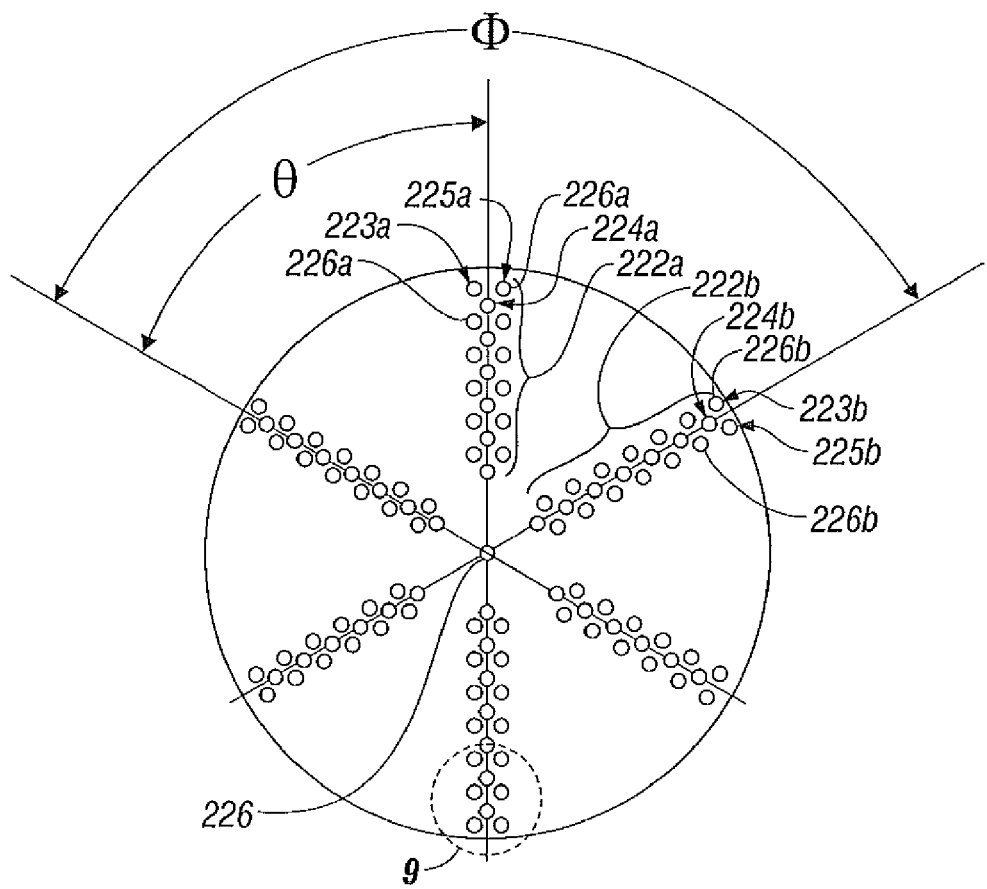
FIG. 8 is a top plan view of the second electrode introducer shown in FIG. 7.
Figure 9:
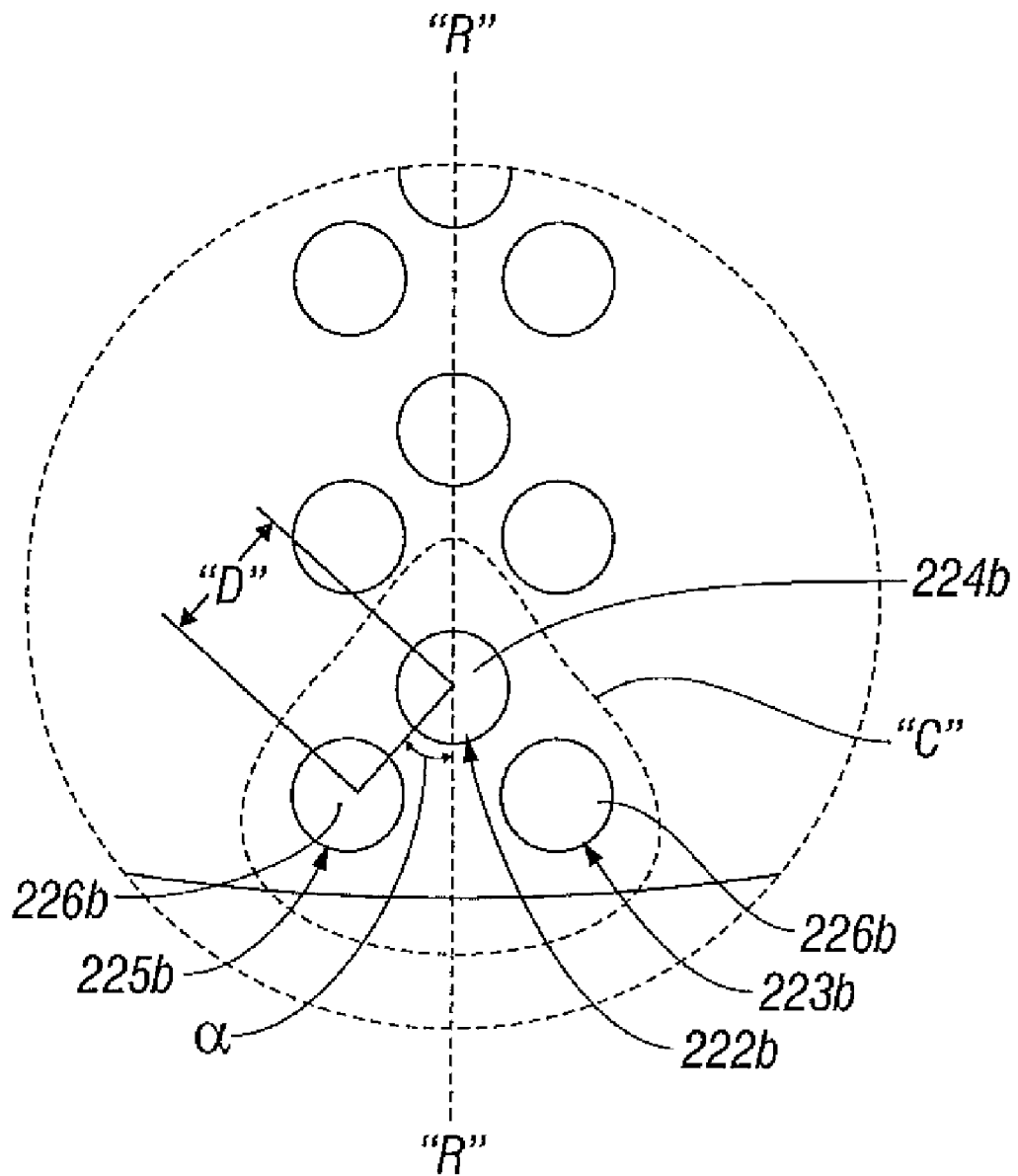
FIG. 9 is an enlarged view of the indicated area of detail of FIG. 8.

Turning now to FIGS. 7-9, distal introducer 220 is similar to proximal introducer 210 and will only be discussed in detail to the extent necessary to identify differences in construction and operation. Distal introducer 220 includes a plurality of radially oriented rows 222 of holes 224 formed therein. Preferably, distal introducer 220 includes six (6) rows 222 of holes 224 which are spaced from one another by an angle "Θ" of approximately 60°. In accordance with an embodiment of the present disclosure, each hole 224 may have a diameter of approximately 0.085 in. (2.16 mm). Preferably, the number and location of holes 224 of distal introducer 220 is substantially identical to the number and location of holes 214 of proximal introducer 210.

As seen in FIGS. 7 and 8, a first set of rows 222a includes six (6) holes 224a formed therealong. Desirably, rows 222a of holes 224a are spaced from one another by an angle "Φ" of approximately 120°. A second set or rows 222b includes seven (7) holes 224b formed therealong. Desirably, rows 222b of holes 224b are spaced from one another by an angle "Φ" of approximately 120°.

As seen in FIGS. 7 and 8, a central hole 226 formed therethrough. Central hole 226 defines a central longitudinal axis "X". Preferably, the central longitudinal "X" axis is at least substantially parallel to the longitudinal axes of holes 224. Desirably, central hole 226 is located at the intersection of rows 222.

As seen in FIGS. 7-9, distal introducer 220 further includes rows 223a and 225a of holes 226a formed on either side of each row of holes 224a the first set of rows 222a and rows 223b and 225b of holes 226b formed on either side of each row of holes 224b of the second set of rows 222b. Desirably, each row 223a and 225a includes six (6) holes corresponding, one each, to holes 224a for each row 222a. Additionally, each row 223b and 225b desirably includes seven (7) holes corresponding, one each, to holes 224b for each row 222b.

As seen in FIGS. 8 and 9, holes 226a, of rows 223a and 225a, and holes 226b, of rows 223b and 225b, are offset a radial distance outward from corresponding holes 224a and 224b, respectively. In particular, a central axis of each hole 226a is desirably spaced a distance "d" from a central axis of a corresponding hole 224b of the first set or rows 222b by an amount of approximately 0.198 in. (5.0 mm) at an angle "α" of approximately 30.00° relative to an axis "R" extending radially through holes 224b (e.g., a diameter or radius of distal introducer 220).

Desirably, radially outer-most holes 226b of rows 223b and 225b and radially outer-most hole 224b of row 222b define a cluster "C" with holes 224b and 226b is a substantially equilateral configuration. As such, cluster "C" may receive three smaller or thinner needles to achieve the same effect as compared to a single larger needle. A plurality of clusters "C" are desirably defines along each row 222a and 222b.

Desirably, a central axis of each hole 226b is also spaced a distance "d" from a central axis of a corresponding hole 224b of the second set or rows 222b by an amount of approximately 0.198 in. (5.0 mm) at an angle "α" of approximately equal to 29.67° relative to an axis "R" extending radially through holes 224a (e.g., a diameter or radius of distal introducer 220).

Desirably, as seen in FIGS. 7 and 8, distal introducer 220 may have a substantially circular geometric profile. In one embodiment, distal introducer 220 may have a diameter of approximately 4.0 in. (102.0 mm). It is further envisioned that distal introducer 220 may have a thickness of approximately 0.375 in. (9.925 mm). While a circular geometric profile is shown, it is envisioned and within the scope of the present disclosure that any geometric profile may be used, such as, for example, hexagonal, rectangular, star-shaped, etc.

It is envisioned that proximal introducer 210 and distal introducer 220 may be fabricated from a rigid, non-conductive material (e.g., plastic, polycarbonate, etc.).

Referring back to FIG. 4, in accordance with one method of use, electrodes 1, 2 and 3 of electrode array system "E" are positioned in holes 214a of rows 212a or in holes 214b of rows 212b, depending on the particular surgical procedure and depending on the size and characteristics of the organ to be operated on. Desirably, electrodes 1, 2 and 3 are placed solely in corresponding holes 214a of rows 212a or in holes 214b of rows 212b. Desirably, electrodes 1, 2 and 3 are positioned in introducer 210 in substantially equilateral triangular configurations. Depending on the size of the target lesion and the particular operative parameters to be employed and/or delivered from electrosurgical generator 16, electrodes 1, 2 and 3 may be placed in holes 214a or 214b which are either closer or further from central hole 216.

Prior to, concomitantly therewith, or subsequent thereto, distal introducer 220 is placed against the body surface of the patient at a location in the proximity to where electrodes 1, 2 and 3 are to be introduced into the body. Desirably, a guide needle 110 (see FIG. 3) extending from the center of distal introducer 220 may be used to position the location of distal introducer 220 relative to the body surface of the patient.

With the relative distance and orientation of electrodes 1, 2 and 3 of electrode array system "E" set by proximal introducer 210 and with distal introducer 220 positioned against the body surface of the patient, electrodes 1, 2 and 3 of electrode array system "E" are then inserted into desired and/or pre-determined holes 224a, 224b of rows 222a or 222b, respectively, or into desires and/or predetermined holes 226a, 226b of rows 223a, 225a or rows 223b, 225b.

Introducer 200, including proximal introducer 210 and distal introducer 220 help to facilitate placement of electrodes 1, 2 and 3 of electrode array system "E" by the clinician. As mentioned above, introducer 200 may function to maintain electrodes 1, 2 and 3 substantially parallel to one another, and at a prescribed spacing relative to one another. The prescribed spacing is determined in part by the energy delivery to the organ which may have an effect on the overall size of the lesion. Additionally, introducer 200 and, in certain instances guide needle 110, aid the clinician in holding electrodes 1, 2 and 3 at the appropriate and/or desired depth and at a substantially equal depth to one another.

It is understood that variations in the choice of electrical output parameters from the electrosurgical generator, to control or monitor the electrode array ablation process, may vary widely depending on the operator's experience, technique, or preference. For example, in the embodiments above, a common RF voltage is applied to all of the electrodes of the array simultaneously. As an alternate embodiment, in accordance with the present disclosure, the clinician may choose to control the RF current to the individual electrodes of the array or the total current of the array as a whole. Voltage variations on each electrode could be applied to achieve constant current output from each electrode. Alternatively, constant power output from each electrode may be sought in some clinical settings. Voltage variations or phases between electrodes may be implemented to achieve desired temperature distribution in the tissue as monitored by temperature sensors in the tissue or by visualization of temperature distribution using thermally sensitive MRI scanning, for example. Accordingly, the choice of electrical output type, sequence, and levels and the distribution of the electrodes of the array should be considered to have wide variations within the scope of the present disclosure.

In view of the foregoing considerations, as would be apparent by persons skilled in the art, implementations and systems should be considered broadly and with reference to the claims set forth below.

What is claimed is:

1. An electrode system for use with a high frequency generator to induce coherent high frequency heat ablation volumes within targeted tissue of a patient, the electrode system comprising:
    at least three electrodes, each including:
        a substantially rigid elongated shaft terminating in a sealed distal end section having an exposed conductive tip portion configured to be inserted into the targeted tissue and adapted at a proximal end section to be coupled to a high frequency generator to simultaneously apply an equal output voltage to each of the exposed conductive tip portions; and
        a closed-loop fluid communication channel pathway which includes an inflow opening adapted for connection to a coolant fluid supply, and a channel portion in fluid communication with the inflow opening, which extends distally inside the conductive tip portion to carry coolant to the inside of the conductive tip portion and further extends proximally back to an outlet opening adapted to carry coolant away from the conductive tip portion;
    an introducer including a plurality of holes defined therein configured to selectively receive a respective elongated shaft of each electrode therethrough, wherein the plurality of holes orient and space each electrode relative to one another; and
    a guide needle disposed at the center of the introducer.

2. The electrode system according to claim 1, wherein the plurality of holes includes a central hole configured to receive the guide needle therethrough.

3. The electrode system according to claim 1, wherein the introducer includes a distal introducer and a proximal introducer, wherein the distal and proximal introducers each include a plurality of holes defined therein including a central hole configured to selectively receive the guide needle therethrough.

4. The electrode system according to claim 3, wherein the proximal introducer is movable relative to the distal introducer and is configured to maintain the electrodes therein during movement to insert the electrodes into tissue.

5. The electrode system according to claim 2, wherein the plurality of holes includes six arrays of holes and each array is arranged in a linear row.

6. The electrode system according to claim 5, wherein the linear rows of holes alternate between rows of six holes and rows of seven holes.

7. The electrode system according to claim 2, wherein the plurality of holes are equally spaced from one another.

8. The electrode system according to claim 2, wherein the plurality of holes includes a plurality of arrays of hole clusters, wherein each array of hole clusters is arranged in a linear row, wherein the rows of hole clusters are equally spaced from one another.

9. The electrode system according to claim 8, wherein each hole cluster includes a radially inner-most hole and a pair of radially outer-most holes, wherein the radially outer-most holes are offset by an angle from an axis extending through the inner-most holes of each respective array of hole clusters.

10. The electrode system according to claim 9, wherein the inner-most holes of each linear row of hole clusters are equally spaced from one another.

11. A method for heat ablation of tissue in a patient, the method comprising:
    providing an electrode system for inducing enlargement of heat ablation volumes within tissue of a patient's body, the electrode system including:
        a high frequency generator for supplying an output voltage;
        at least three substantially rigid, elongated electrodes adapted to be inserted into the tissue of a patient's body, each of the at least three electrodes including an exposed conductive tip portion and a closed-loop fluid communication channel pathway, which includes an inflow opening adapted for connection to a coolant fluid supply and a channel portion in fluid communication with the inflow opening, the channel portion extending distally inside the conductive tip portion to carry coolant to the inside of the conductive tip portion and further extending proximally back to an outlet opening adapted to carry coolant away from the conductive tip portion, wherein the exposed conductive tip portions of the at least three electrodes are arranged in a predetermined parallel relationship with each other; and
        an introducer including a plurality of holes defined therein configured to selectively receive a respective elongated shaft of each electrode therethrough, wherein the plurality of holes orient and space each electrode relative to one another, wherein the introducer includes a central hole defined therein configured to receive a guide needle therethrough;
    advancing a guide needle through the central hole of the introducer;
    inserting the electrodes into desired holes of the introducer to position each electrode relative to one another;
    inserting the electrodes into tissue;
    applying substantially the same radio frequency output through the electrodes to a targeted tissue volume to produce coherent heating of the targeted tissue volume;
    raising the radio frequency output to a level that induces enlargement of the volume of heat ablation in tissue near the electrodes; and
    cooling each electrode by circulating a cooling fluid through the closed-loop fluid communication channel pathway formed in each of the electrodes.

12. The method according to claim 11, further comprising:
    inserting the guide needle into the patient's body such that a tip of the guide needle is placed in close proximity to a targeted tissue.

13. The method according to claim 12, further comprising:
    withdrawing the guide needle from the introducer, wherein the guide needle is advanced through the central hole of the introducer prior to withdrawing the guide needle from the introducer.

14. An introducer for facilitating insertion of a cluster of electrodes into the body of a patient for performing tissue ablation, the introducer comprising:

a body portion including a plurality of holes defined therein configured to selectively receive a respective elongated shaft of the electrodes therethrough, wherein the plurality of holes of the body portion are configured to orient and space each electrode relative to one another; and
a guide needle disposed at the center of the body portion,
wherein the plurality of holes includes a central hole configured to receive the guide needle,
wherein the body portion includes:
    a distal body portion including a plurality of arrays of holes defined therein, wherein each array of holes is arranged in a linear row, wherein the rows of holes are equally spaced from one another; and
    a proximal body portion including a plurality of arrays of holes defined therein, wherein each array of holes is arranged in a linear row, wherein the rows of holes are equally spaced from one another, and
wherein the proximal body portion is movable relative to the distal body portion to insert the electrodes into tissue.

15. The introducer according to claim 14,
wherein the proximal body portion includes six arrays of holes formed therein,
wherein the holes of each linear row of holes of the proximal body portion are equally spaced from one another, and
wherein the rows of holes of the proximal body portion alternate between rows of six holes and rows of seven holes.

16. The introducer according to claim 15, wherein each array of holes of the distal body portion includes a radially inner-most hole and a pair of radially outer-most holes, wherein the radially outer-most holes are offset by an angle from an axis extending through the inner-most holes of each respective array of holes.

\* \* \* \* \*